United States Patent
Fening et al.

(10) Patent No.: US 9,949,761 B2
(45) Date of Patent: Apr. 24, 2018

(54) NONINVASIVE DEVICE FOR ADJUSTING FASTENER

(71) Applicants: Austen BioInnovation Institute in Akron, Akron, OH (US); Children's Hospital Medical Center of Akron, Akron, OH (US)

(72) Inventors: Stephen D. Fening, Willoughby Hills, OH (US); Todd Ritzman, Akron, OH (US)

(73) Assignees: CHILDREN'S HOSPITAL MEDICAL CENTER OF AKRON, Akron, OH (US); AUSTEN BIONNOVATION INSTITUTE IN AKRON, Akron, OH (US)

( * ) Notice: Subject to any disclaimer, the term of this patent is extended or adjusted under 35 U.S.C. 154(b) by 537 days.

(21) Appl. No.: 13/712,387

(22) Filed: Dec. 12, 2012

(65) Prior Publication Data
US 2013/0150889 A1 Jun. 13, 2013

Related U.S. Application Data

(60) Provisional application No. 61/569,453, filed on Dec. 12, 2011, provisional application No. 61/585,450, filed on Jan. 11, 2012.

(51) Int. Cl.
*A61B 17/70* (2006.01)
(52) U.S. Cl.
CPC ........ *A61B 17/7022* (2013.01); *A61B 17/707* (2013.01); *A61B 17/7016* (2013.01)

(58) Field of Classification Search
CPC . A61B 17/70–17/7046; A61B 17/84–17/8695; Y10T 403/7005–403/7011
(Continued)

(56) References Cited

U.S. PATENT DOCUMENTS

RE24,066 E * 10/1955 Brown ............................ 81/125
5,575,790 A 11/1996 Chen et al.
(Continued)

FOREIGN PATENT DOCUMENTS

CN 101466321 A 6/2009
DE 19807663 A1 9/1999
(Continued)

OTHER PUBLICATIONS

INVIS (North America), Inc., INVIS Invisible, detachable joining. Brochure, 2010, 6 pages.
(Continued)

*Primary Examiner* — Jan Christopher Merene
*Assistant Examiner* — Steven Cotroneo
(74) *Attorney, Agent, or Firm* — Tucker Ellis LLP; Heather M. Barnes; Michael G. Craig

(57) ABSTRACT

One or more techniques and/or systems are disclosed for a system for noninvasive adjusting fastener tensioning has an elongated shaft having a slot defined therein. The shaft has a first end oppositely disposed from the second end. An associated rod or rods may pass through each end. Selectively adjustable fasteners may have a plurality of magnets disposed in the head of the fastener. An external drive device generating a magnetic field may be used to rotate the fasteners via the magnets in the fastener head externally without the need for surgery. The fasteners may move in and out from the shaft and contact the rod to adjust tensioning.

11 Claims, 18 Drawing Sheets

(58) Field of Classification Search
USPC .................................... 606/246–279, 86 A
See application file for complete search history.

(56) References Cited

U.S. PATENT DOCUMENTS

| | | | |
|---|---|---|---|
| 5,704,939 A | 1/1998 | Justin | |
| 6,004,349 A * | 12/1999 | Jackson | 606/270 |
| 6,033,412 A | 3/2000 | Losken et al. | |
| 6,514,255 B1 * | 2/2003 | Ferree | 606/263 |
| 6,849,076 B2 | 2/2005 | Blunn et al. | |
| 7,650,888 B2 | 1/2010 | Maschke | |
| 7,753,915 B1 * | 7/2010 | Eksler et al. | 606/105 |
| 7,763,053 B2 | 7/2010 | Gordon | |
| 7,862,502 B2 | 1/2011 | Pool et al. | |
| 7,955,357 B2 | 6/2011 | Kiester | |
| 7,963,978 B2 * | 6/2011 | Winslow | A61B 17/7005 |
| | | | 128/898 |
| 7,981,025 B2 | 7/2011 | Pool et al. | |
| 8,016,837 B2 * | 9/2011 | Giger | A61B 17/8076 |
| | | | 606/105 |
| 8,057,472 B2 | 11/2011 | Walker et al. | |
| 8,197,490 B2 | 6/2012 | Pool et al. | |
| 8,240,942 B2 | 8/2012 | Baur et al. | |
| 8,343,192 B2 | 1/2013 | Kiester | |
| 8,382,756 B2 | 2/2013 | Pool et al. | |
| 8,419,734 B2 | 4/2013 | Walker et al. | |
| 8,529,609 B2 * | 9/2013 | Helgerson et al. | 606/306 |
| 8,568,457 B2 | 10/2013 | Hunziker | |
| 8,632,548 B2 | 1/2014 | Soubeiran | |
| 8,852,236 B2 | 10/2014 | Kiester | |
| 9,011,499 B1 | 4/2015 | Kiester | |
| 2004/0030395 A1 | 2/2004 | Blunn et al. | |
| 2004/0236329 A1 | 11/2004 | Panjabi | |
| 2004/0254575 A1 | 12/2004 | Obenchain et al. | |
| 2005/0090827 A1 * | 4/2005 | Gedebou | 606/72 |
| 2006/0047282 A1 * | 3/2006 | Gordon | 606/61 |
| 2006/0058792 A1 * | 3/2006 | Hynes | 606/61 |
| 2006/0074448 A1 | 4/2006 | Harrison et al. | |
| 2006/0079897 A1 | 4/2006 | Harrison et al. | |
| 2006/0229615 A1 * | 10/2006 | Abdou | 606/61 |
| 2007/0233098 A1 * | 10/2007 | Mastrorio et al. | 606/61 |
| 2007/0270803 A1 | 11/2007 | Giger et al. | |
| 2007/0276378 A1 | 11/2007 | Harrison et al. | |
| 2008/0027436 A1 * | 1/2008 | Cournoyer | A61B 17/7014 |
| | | | 606/250 |
| 2008/0033436 A1 | 2/2008 | Song et al. | |
| 2009/0005821 A1 * | 1/2009 | Chirico et al. | 606/319 |
| 2009/0012565 A1 | 1/2009 | Sachs et al. | |
| 2009/0082815 A1 * | 3/2009 | Zylber et al. | 606/295 |
| 2009/0112262 A1 | 4/2009 | Pool et al. | |
| 2009/0112263 A1 | 4/2009 | Pool et al. | |
| 2009/0198273 A1 * | 8/2009 | Zhang et al. | 606/205 |
| 2009/0198279 A1 * | 8/2009 | Zhang et al. | 606/264 |
| 2009/0204154 A1 | 8/2009 | Kiester | |
| 2010/0094303 A1 * | 4/2010 | Chang et al. | 606/90 |
| 2010/0094306 A1 | 4/2010 | Chang et al. | |
| 2010/0111599 A1 | 5/2010 | Baur et al. | |
| 2010/0114103 A1 | 5/2010 | Harrison et al. | |
| 2010/0121323 A1 | 5/2010 | Pool et al. | |
| 2010/0137911 A1 * | 6/2010 | Dant | 606/252 |
| 2010/0217271 A1 | 8/2010 | Pool et al. | |
| 2010/0280551 A1 | 11/2010 | Pool et al. | |
| 2011/0060336 A1 | 3/2011 | Pool et al. | |
| 2011/0137347 A1 | 6/2011 | Hunziker | |
| 2012/0035656 A1 | 2/2012 | Pool et al. | |
| 2012/0035661 A1 | 2/2012 | Pool et al. | |
| 2012/0130428 A1 | 5/2012 | Hunziker | |
| 2013/0150889 A1 | 6/2013 | Fening et al. | |
| 2014/0296919 A1 * | 10/2014 | Culbert | A61B 17/7016 |
| | | | 606/272 |
| 2014/0371796 A1 | 12/2014 | Kiester | |

FOREIGN PATENT DOCUMENTS

| | | |
|---|---|---|
| DE | 20013178 U1 | 11/2000 |
| DE | 202008016178 U1 | 4/2009 |
| DE | 202008016179 U1 | 4/2009 |
| DE | 102009042844 A1 | 9/2010 |
| DE | 102009043179 A1 | 9/2011 |
| EP | 2602494 A1 | 6/2013 |
| JP | 2009-532190 A | 9/2009 |
| JP | 2011-502003 A | 1/2011 |
| WO | 2004/019796 A1 | 3/2004 |
| WO | 2007/118179 A2 | 10/2007 |
| WO | 2008/135250 A2 | 11/2008 |
| WO | 2009/058546 A1 | 5/2009 |
| WO | 2012021378 A2 | 2/2012 |
| WO | 2012021378 A3 | 2/2012 |

OTHER PUBLICATIONS

Crown Heritage, Crown Heritage—EasAlign. Brochure, 2012, 3 pages.
PCT International Search Report and Written Opinion from International Application No. PCT/US2012/069118, dated Feb. 26, 2013, 14 pages.
PCT International Preliminary Report on Patentability, International Application PCT/US2012/069118, dated Jun. 26, 2004, 9 pages.
Pot International Search Report and Written Opinion from International Application No. PCT/US2015/035597, dated Sep. 1, 2015, 15 pages.

* cited by examiner

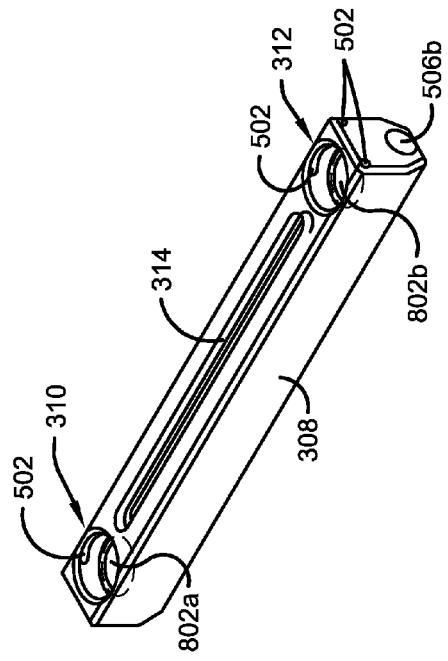
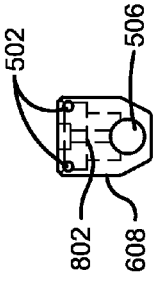
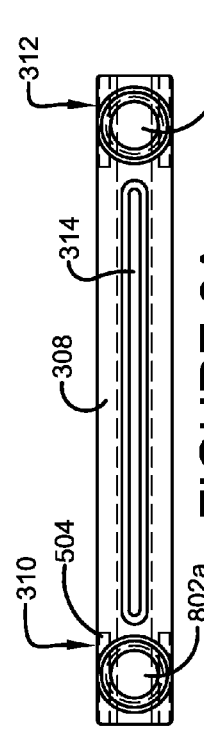
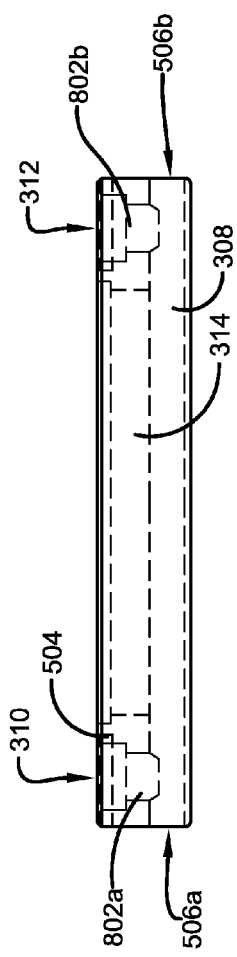
FIGURE 8C
FIGURE 8D
FIGURE 8A
FIGURE 8B

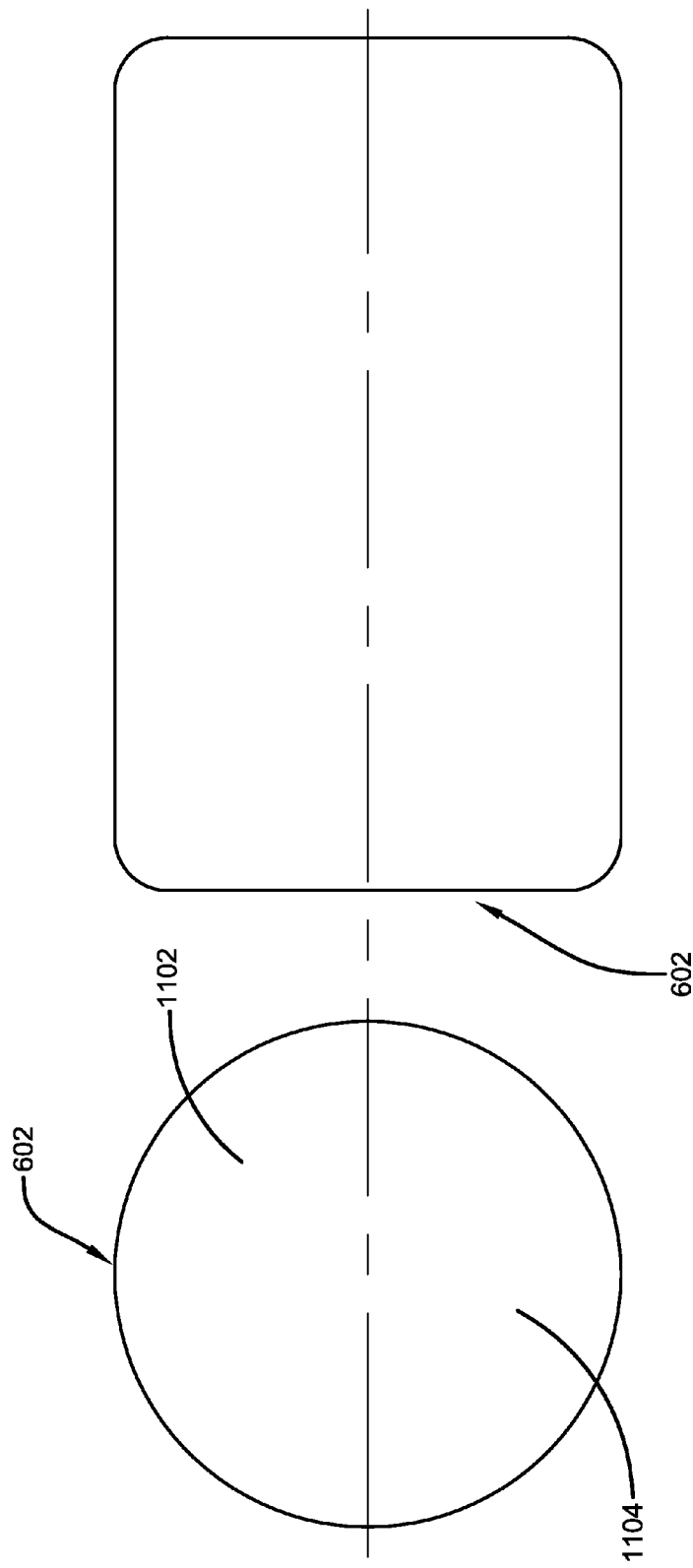

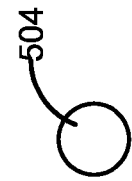
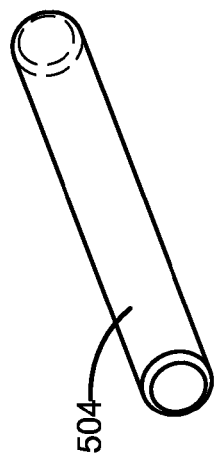
FIGURE 12B
FIGURE 12C
FIGURE 12A

DETAIL C

NONINVASIVE DEVICE FOR ADJUSTING FASTENER

CROSS-REFERENCE TO RELATED APPLICATIONS

This application claims the benefit of U.S. Provisional Application No. 61/569,453, filed Dec. 12, 2011; and this application claims the benefit of U.S. Provisional Application No. 61/585,450, filed Jan. 11, 2012. All of the subject matter disclosed by U.S. Provisional Application No. 61/569,453 and U.S. Provisional Application No. 61/585,450 is hereby incorporated by reference into this application.

BACKGROUND

Early-onset scoliosis (EOS) can affect children before they have reached skeletal maturity. If left untreated, it can cause damaging spinal deformity early in life, which, in turn, can affect other aspects of the child's health, such as lung performance. For example, if the spine continues to deform during growth, an area available for the lungs may not keep pace with the respiratory needs of the child. Thus, early treatment of this condition can be vital to a child's future health and well-being. Typically, growing rods are surgically engaged with the patient's spine, and periodically adjusted (e.g., lengthened), for example, to provide correction of deformity and tension to stimulate growth of the spine to help in the treatment of scoliosis. However, the periodic adjustments (e.g., typically every six months) require surgery to manipulate the implanted growth rods.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

As provided herein, a noninvasive spinal tensioning device may be utilized in the treatment of scoliosis. For example, an elongated rod holder may have a first end oppositely disposed from a second end, where an associated rod or rods may pass through respective ends of the holder. One or more magnetically, selectively adjustable fasteners, such as set screws, can be used to secure the rod(s) in the rod holder. In one example, an external device may generate a desired magnetic field that can cause the fastener(s) to loosen and/or tighten, thereby allowing for adjustment of the rod(s), without a need for surgery.

In one implementation, a noninvasive tensioning device may comprise a rod holder comprising a first end and a second end, where the rod holder can be configured to hold at least a first rod. The noninvasive tensioning device may further comprise a first fastener that can be disposed at the first end of the rod holder. The first fastener can be operably coupled with a first magnet that may be configured to apply torque to the first fastener when subjected to a desired magnetic field. Additionally, the first fastener can be configured to secure the first rod with respect to said rod holder.

To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

BRIEF DESCRIPTION OF THE DRAWINGS

The invention may take physical form in certain parts and arrangement of parts, a preferred implementation of which will be described in detail in this specification and illustrated in the accompanying drawings which form a part hereof and wherein:

FIGS. 8A, 8B, 8C, and 8D are component diagrams illustrating various views of an example implementation of one or more portions of one or more systems described herein.

FIGS. 11A and 11B are component diagrams illustrating various views of an example implementation of one or more portions of one or more systems described herein.

FIGS. 12A, 12B, and 12C are component diagrams illustrating various views of an example implementation of one or more portions of one or more systems described herein.

DETAILED DESCRIPTION

Figure 1:
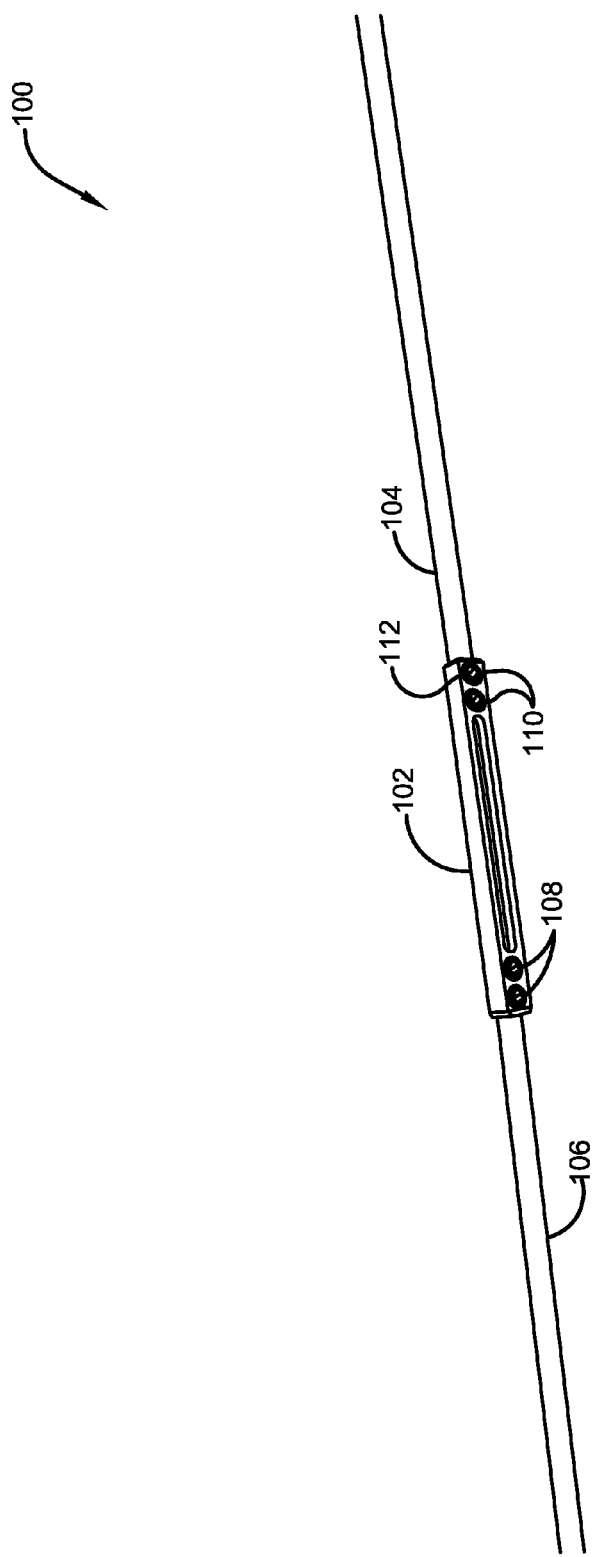
FIG. 1 illustrates a perspective view of an example growing rod apparatus.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices may be shown in block diagram form in order to facilitate describing the claimed subject matter.

Typically, an initial management of scoliosis and other spinal deformities is undertaken using serial casting followed by bracing. If such treatment is not feasible, or not successful, surgical management is often warranted. Spinal fusion is a common form of surgical treatment for progressive scoliosis in adults and skeletally mature children. Spinal fusion usually involves placement of rods, hooks, pedicle screws, and/or bone grafts to correct the affected portion of the spine. However, this type of surgery can immobilize the treated sections of the spine. When a child is skeletally immature, spinal fusion treatment can limit the potential growth of the child, which may lead to other potential health problems, such as thoracic insufficiency syndrome, in which reduced or halted growth of the thorax may fail to provide sufficient volume for healthy adult respiratory function.

Some current options may allow for both scoliosis correction and future growth. Growth-sparing treatments, which may utilize dual growing rods (DGR) and/or vertical expandable prosthetic titanium rib (VEPTR), can provide for treatment of the scoliosis condition and may allow for continued thoracic growth. Conceptually, rods can be anchored to bones, including the spine, the rib, and/or the pelvis, and the rods are configured to be selectively lengthened. However, patients undergoing these treatments typically need repetitive surgical interventions to first implant, and subsequently lengthen the implants, sometimes as often as every four months.

FIG. 1 illustrates a perspective view of an example growing rod apparatus 100. As one example, some existing growth rod devices used to treat scoliosis in humans comprise a rod holder 102, one or more growth rods 104, 106, and one or more pairs of set screws 108, 110 used to secure the rod(s) 104, 106 to the rod holder 102. Typically, the set screws 108, 110 comprise a tool engagement opening 112 that is designed to receive a tool used to loosen and/or tighten the screw. For example, a hex-tool (e.g., allen-wrench) may be inserted into the tool engagement opening 112 and rotated (e.g., clock-wise, counter clock-wise) to loosen and/or tighten the screw 108, 110.

Further, for example, in order to access the tool engagement opening 112 of the example growth rod apparatus 100, when the growth rod apparatus 100 is implanted in a patient, the patient needs to undergo invasive surgery (e.g., be cut open). In one implementation, when an adjustment of the example growth rod apparatus 100 is undertaken for young, skeletally immature patients, an open spinal surgery may be needed every six months until the age of skeletal maturity. Not only can these multiple surgeries pose a significant morbidity from the surgery alone, for example, but a severe psychosocial hurdle may be imposed, particularly for the skeletally immature and their care givers. While other complications to this type of treatment may arise, morbidity typically arises from the need for repeated surgical intervention. Infections and skin-related complications may lead to additional surgeries, long term antibiotics therapy, and psychosocial stress from chronic hospitalization on both the patient and the care-giver.

Figure 2:
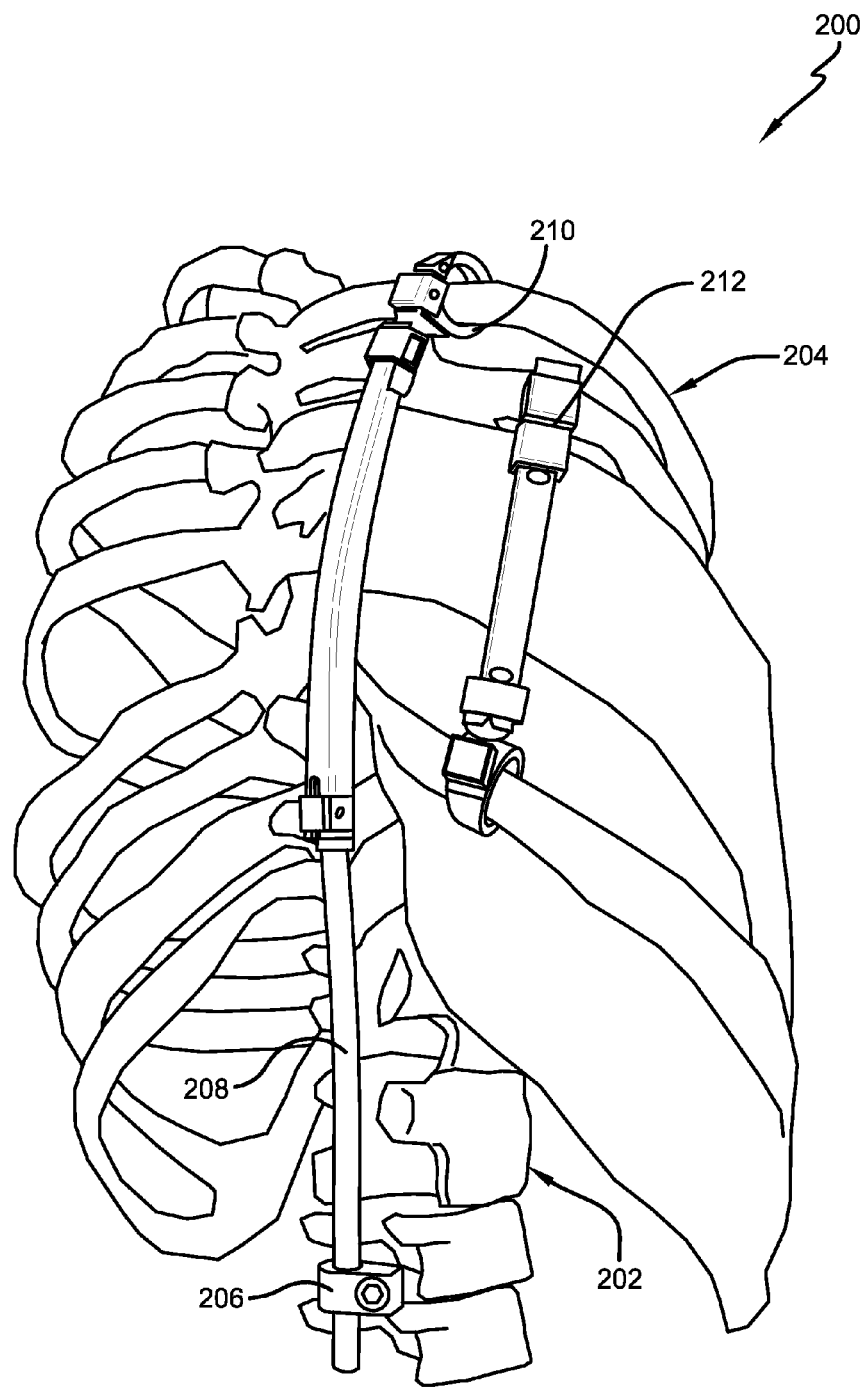
FIG. 2 illustrates a perspective view of another example growing rod apparatus.
Figure 3:
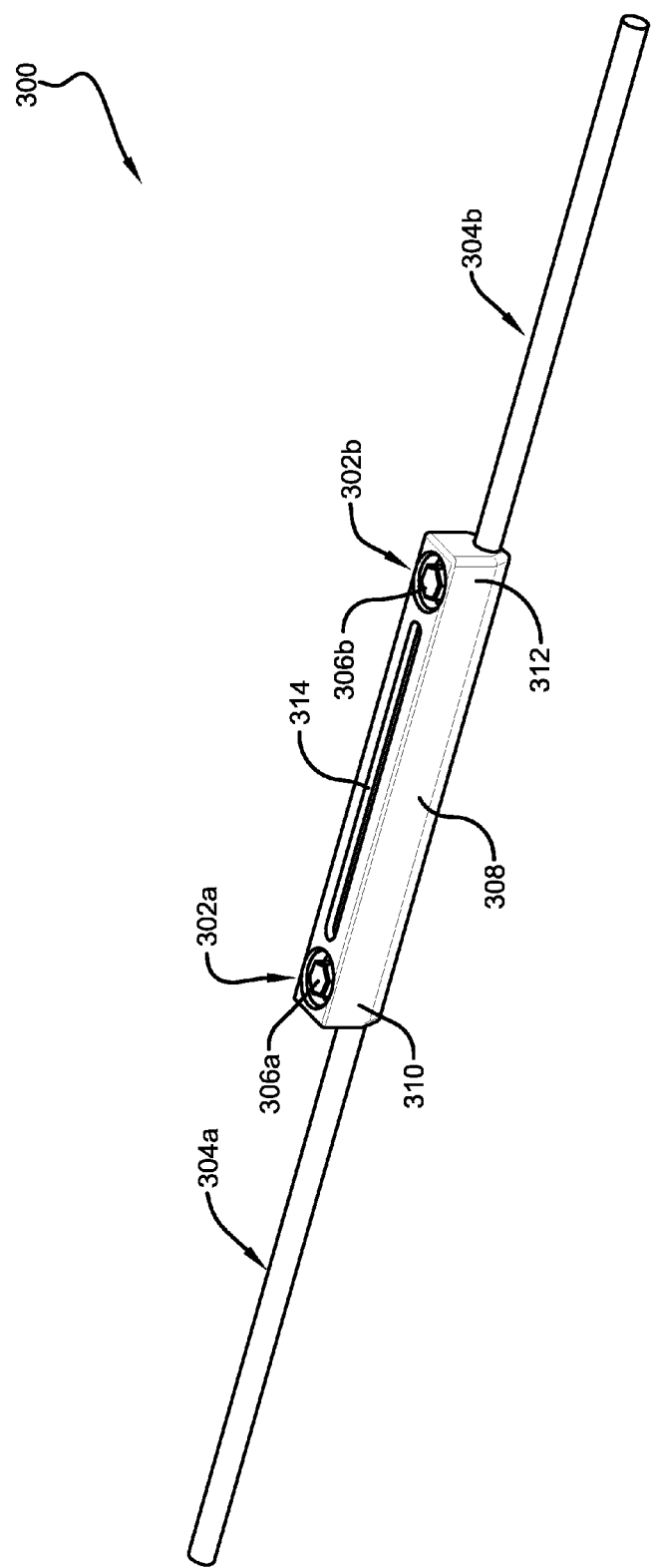
FIG. 3 a component diagram illustrating a perspective view of one or more portions an exemplary growth rod in accordance with one or more systems described herein.

FIG. 2 illustrates a perspective view of one implementation 200 of an example of a growing rod apparatus. In this example 200, a first type of growing rod system 208 may be engaged with (e.g., screwed into) a patient's spine 202 at a first end 206, and with the patients ribcage 204 at a second end 210. As one example, by securing the example, device 208 to the spine 202 and ribcage 204, a desired orientation of the patient's spine 202 may be obtained. Further, the desired orientation may be adjusted periodically, by surgically opening the patient and manually manipulating the device 208, for example, in order to adjust the spine to a desired final orientation. As another example, a second type of growth rod system 212 may be merely engaged with the patient's ribcage 204; however, manual manipulation via invasive surgery may still be needed.

Accordingly, as described herein, a non-invasive system and/or device may be devised that can provide a treatment for scoliosis, may allow for continued thoracic growth, and may mitigate repetitive surgical interventions. As one example, a system may utilize one or more rods respectively secured to a rod holder by one or more fasteners, where respective fasteners can be tightened and/or loosened by an external device (e.g., without surgical intrusion of the patient). That is, for example, a fastener can be coupled with a magnetic component that may be rotated by the external device. In this example, when the magnetic component rotates it may apply torque to the fastener, thereby tightening and/or loosening the fastener. Further, the fastener may be situated in the rod holder such that tightening the fastener can secure a corresponding rod, with respect to the rod holder. In one implementation, adjustment procedures for such a non-invasive device may be undertaken an exam room, for example, instead of an operating room.

Referring now to the drawings, which are for the purpose of illustrating implementations of a non-invasive system and/or device, and not for purposes of limiting the same, with reference to FIGS. 3-6, a system and/or device 300 for non-invasive tensioning, such as of an implanted growing rod treatment, is described. The non-invasive tensioning system 300 comprises a rod holder 308 comprising a first end 310 and a second end 312. The rod holder 308 is configured to selectively engage with a first rod 304a. Further, the non-invasive tensioning system 300 comprises a first fastener 302a disposed at the first end 310. The first fastener 302a is configured to secure the first rod 304a with respect to the rod holder 308. Additionally, the non-invasive tensioning system 300 comprises a first magnet component 602a that is operably coupled with the first fastener 302a. The first magnet component 602a is configured to apply torque to the first fastener 302a when it is subjected to a desired magnetic field.

In one implementation, the non-invasive tensioning system 300 can comprise a second fastener 302b disposed at the second end 312 of the rod holder 308. The second fastener 302b can be configured to secure a second rod 304b with respect to said rod holder 308. In one implementation, the second fastener 302b may be configured to secure the first rod 304a to the rod holder 308, for example, where the first rod 304a extends from the first end 310 to the second end 312 of the rod holder (e.g., through an entire length of the rod holder 308). Further, the non-invasive tensioning system 300 can comprise a second magnet component 602b, that is operably coupled with the second fastener 302b. The second magnet component 602b can be configured to apply torque to the second fastener 302b when it is subjected to the desired magnetic field.

As one example, using the magnet component 602 to loosen and/or tighten the fastener holding the rod in the rod holder may enables the exemplary tensioning system 300 (e.g., growing rod apparatus) to be re-tensioned without needing to gain direct, surgical access to heads 306 of the fasteners 302. In one implementation, the fasteners 302 may be rotated (e.g., loosened or tightened) by applying a desired magnetic field to the magnetic components 602. It should be understood that a magnetic field may induce a force upon certain components as described herein. As used herein the force induced by the magnetic field will be referred to as magnetic force. Further, in one implementation, the desired magnetic field can comprise a magnetic field that provides a desired amount of magnetic force in a desired orientation, for example, that cause the fastener to rotate in a desired direction (e.g., clockwise, counter-clockwise).

With continued reference to FIGS. 3-6, and further reference to FIGS. 7-13, the rod holder 308 of the exemplary system/device 300 can comprise a rod receiving shaft 506, sleeve, tube or any aperture that is entirely hollow or partially hollow. In one implementation, the rod holder 308 (e.g., as illustrated in FIGS. 8B and 8C) can comprise a first rod receiving shaft 506a with an opening at the first end 310, where the first rod receiving shaft portion 506a is configured to selectively engage the first rod 304a. Further, the rod holder 308 can comprise a second rod receiving shaft portion 506b with an opening at the second end 312, where the second rod receiving shaft portion 506b is configured to selectively engage the second rod 304b.

In one implementation, the first rod receiving shaft portion 506a and the second rod receiving shaft portion 506b may be disposed along a same shaft axis, for example, such that the first rod receiving shaft portion 506a and second rod receiving shaft portion 506b may form a continuous rod receiving shaft 506 through the rod holder 308. An elongated slot 314 can be disposed between the first end 310 and the second end 312. In one implementation, the first rod receiving shaft portion 506a and the second rod receiving shaft portion 506b may intersect the elongated slot 314, for example, such that the first rod 304a and/or the second rod 304b may be visible through an opening of the elongated slot 314 (e.g., to visibly determine a location of respective rods engaged in the shaft(s)).

In one implementation, the first rod receiving shaft portion 506a may lie along a first shaft axis and the second rod receiving shaft portion 506b may lie along a second shaft axis. As one example, the first and second shaft axes may be offset with respect to the rod holder 308. That is, for example the first rod receiving shaft portion 506a may run along the length of the rod holder 308 on a first side, while the second rod receiving shaft portion 506b may run along the length of the rod holder 308 on a second side. In this example, the first rod 304a can engage the first rod receiving shaft portion 506a, and the second rod 304b can engage the second rod receiving shaft portion 506b, and the two rods may not meet inside the rod holder, and they may extend completely through the length of the rod holder 308.

In one implementation, multiple fasteners may be disposed at respective ends 310, 312 of the rod holder 308 (e.g., as in FIG. 1). That is, for example, one or more additional fasteners can be disposed at the first end 310, along with the first fastener 302a. The one or more additional fasteners can also be configured to secure the first rod 304a with respect to the rod holder 308. Further, two or more second fasteners (e.g., the second fastener 302b and one or more additional fasteners) can be disposed at the second end 312, and can also be configured to secure the second rod 304b with respect to the rod holder 308.

Figure 4:
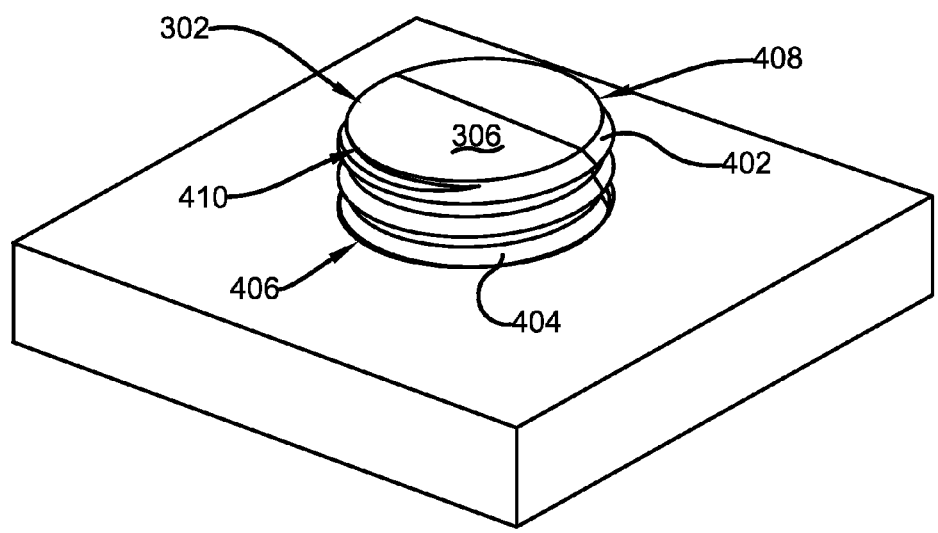
FIG. 4 is a component diagram illustrating a perspective view of an example implementation of one or more portions of one or more systems described herein.

As illustrated in FIGS. 3-13, respective fasteners 302 may comprise screw head 306, a screw shank 402, and a threaded portion 404. In one implementation, as illustrated in FIG. 4, the threaded portion 404 may be configured to be received by, and engage with, a threaded receiving portion 406, for example, disposed in the rod holder 308, such as at the first end 310 and/or the second end 312. In one implementation, the magnet component 602 may be operably coupled with the fastener 302 (e.g., such as at the screw shank 402), such that a north pole portion of the magnet component 602 resides at a first side 408 of the fastener 302, and a south pole portion of the magnet component 602 resides at a second side 410 of the fastener 302. In this way, for example, a north pole magnetic force applied to the first side 408 of the fastener 302 may cause the fastener 302 to rotate in a desired direction; and a south pole magnetic force applied to the second side 410 of the fastener 302, may cause the fastener 302 to continue to rotate in the desired direction. Further, if the application of the north pole and the south pole force is continuously alternated (e.g., rotationally), the fastener 302 may continue to rotate in the desired direction.

Figure 6:
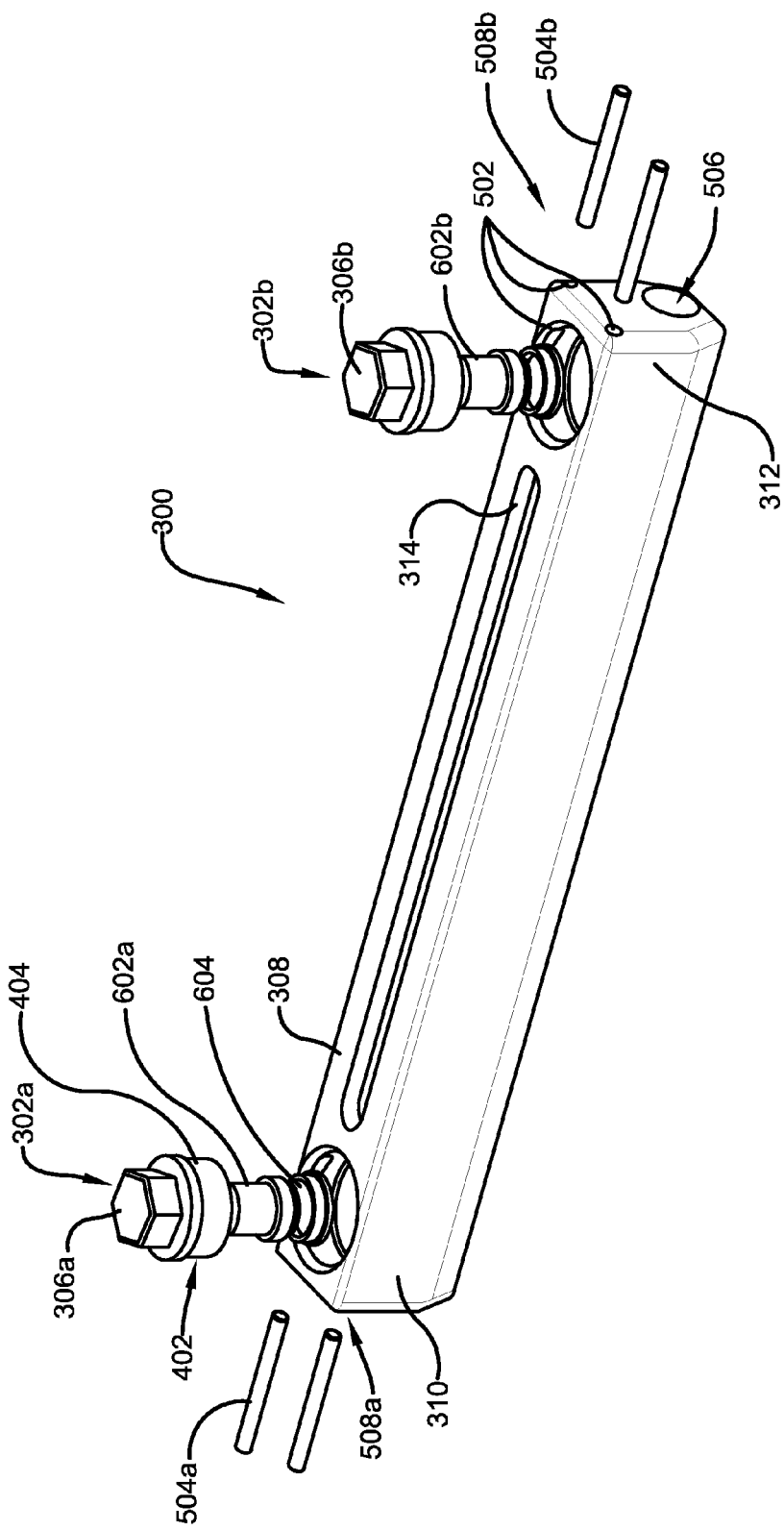
FIG. 6 is a component diagram illustrating an exploded view of an example implementation of one or more portions of one or more systems described herein.

In another implementation, the magnet component 602 may be disposed in rotational engagement with at least a portion of the fastener 302. As one example, as illustrated in FIG. 6, the first magnet component 602a may be rotationally engaged with the screw shank 402 of the first fastener 302a, and the second magnet component may be rotationally engaged with the screw shank 402 of the second fastener 302b. As further illustrated in FIGS. 7 and 9A-D, the geometry of the fastener(s) 302 may be any form chosen with sound engineering judgment. In one implementation, the screw shank 402 may comprise a cylinder form. Further, the fastener 302 can comprise an interior portion 902, in which the magnet component 602 may be disposed, in rotational engagement with the fastener's shank 402.

In one implementation, the magnet component 602 (e.g., comprising one or more magnets) may be free floating or seated inside the interior portion 902, such that they are not fixedly engaged with any portion of the interior 902. In one example, the magnet component 602, as illustrated in FIGS. 11A and 11B, comprising opposite north 1102 and south 1104 poles, may freely rotate inside the interior portion 902 when subjected to the desired magnetic field, as described above.

With reference to FIGS. 7, 9A-D, 10A-D, and 11A-B, in one implementation, the fastener may comprise a magnet engaging component 904, such as an extension disposed in the interior portion 902 of the screw shank 402, that is engaged with the first fastener. In one implementation, the magnet engaging component 904 may be formed with the fastener 302; and in another implementation, the magnet engaging component 904 may be attached to the fastener 302. The magnet engaging component 904 can be configured to selectively engage with the magnet component 602, such that an application of torque to the first magnet component 602 that is engaged with the magnet engaging component 904 causes torque to be applied to the fastener 302.

In one implementation, the magnet component 602 may comprise a collar extension 702, which extends from a magnet collar 704 fixedly engaged with the magnet component 602. For example, the magnet collar component 704 may comprise an annular shape configured to merely fit around the magnet component 602 in fixed engagement. In one implementation, the magnet collar component 704 may be formed with the magnet component 602; in another implementation the magnet collar component 704 may be attached (e.g., press fit, adhered, glued, welded, soldered, etc.) to the magnet component 602. Further, the magnet collar component 704 can comprise the collar extension 702, which is configured to be disposed in opposing engagement with respect to the interior extension 904 disposed in the interior portion 902 of the screw shank 402.

As one example, as a magnetic force (e.g., as the desired magnetic field) is applied to the magnet component 602, the magnet component can rotate (e.g., in a direction dependent on the rotation of the desired magnetic field, as described above), and the collar extension 702 can engage the interior extension portion 904 of the fastener 302, which may cause the fastener 302 to rotate in the same direction of rotation. In one implementation, the interior portion 902 may comprise a track for the magnet component (e.g., and/or magnet collar 704) to improve engagement of the collar extension 704 with magnet engaging component 904 (e.g., interior portion extension), in order to provide the appropriate torque to the fastener 302.

In one aspect, when the magnetic force provided by the desired magnetic field causes the magnet component 602 (e.g., the collar extension 704 of the magnet collar 702) to engage the magnet engaging component 904 of the fastener 302, the magnet component 602 may rebound (e.g., bounce back from engagement), depending on an amount of rotational resistance extant for the fastener. In one implementation, upon the magnet component 602 disengaging (e.g., bouncing away from) the magnet engaging component 904, when the fastener encounters a certain amount of rotational resistance (e.g., stops rotating), the magnet component 602 can re-engage the magnet engaging component 904, when the magnet component 602 is subjected to the desired magnetic field. In this implementation, when the magnet component 602 re-engages the magnet engaging component 904, a rotational hammering force may be applied to the fastener 302.

As an example, the magnetic force provided by the desired magnetic field can be re-applied to the magnet component 602, causing it to re-contact the collar extension 702 of the magnet collar 704 within the screw shank 402 of the fastener 302. In this example, a repeated bounce-back and re-engagement action can cause a type of hammering effect between the collar extension 702 and the magnet engaging component 904 (e.g., the interior extension of the screw shank 402). It may be the hammering action, for example, that can cause the fastener 302 to rotate, particularly when subjected to rotational resistance. In this way, for example, a loose screw may be tightened more effectively, and a tight screw may be loosened more effectively.

Figure 7:
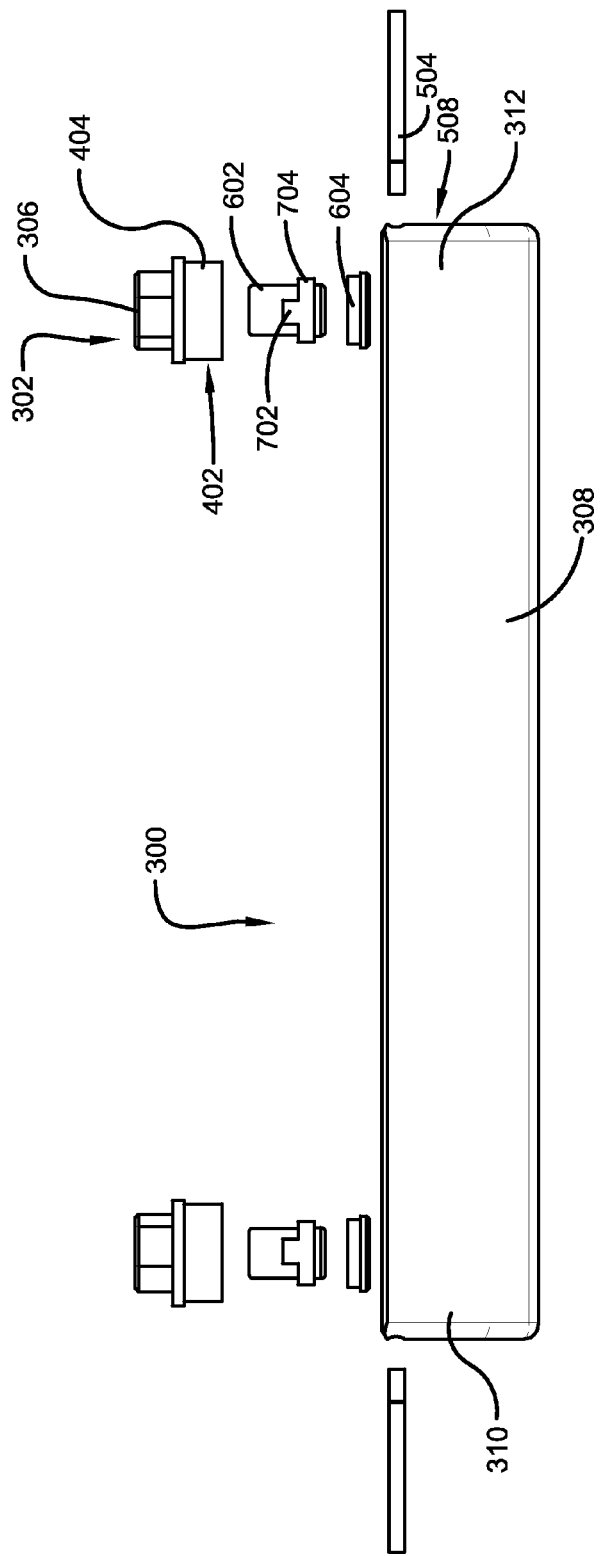
FIG. 7 is a component diagram illustrating an exploded view of an example implementation of one or more portions of one or more systems described herein.
Figure 9A:
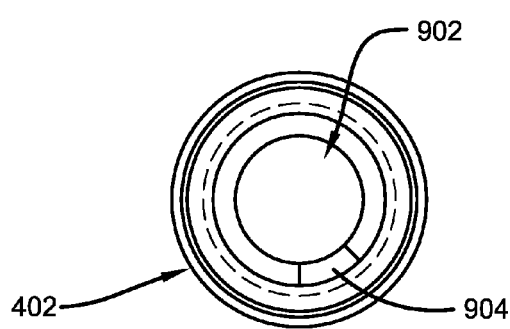
FIGS. 9A, 9B, 9C, and 9D are component diagrams illustrating various views of an example implementation of one or more portions of one or more systems described herein.
Figure 9C:
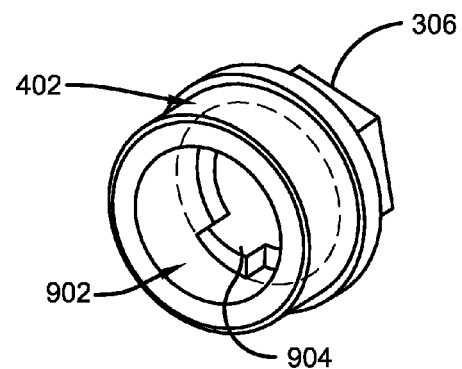
Figure 9B:
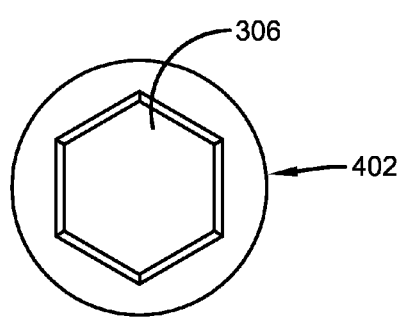
Figure 9D:
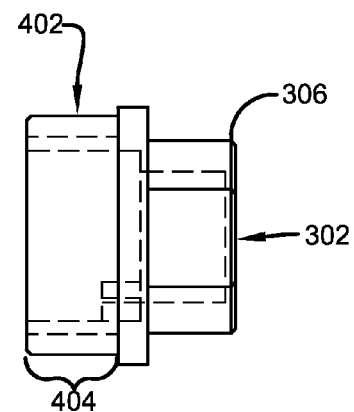
Figure 10C:
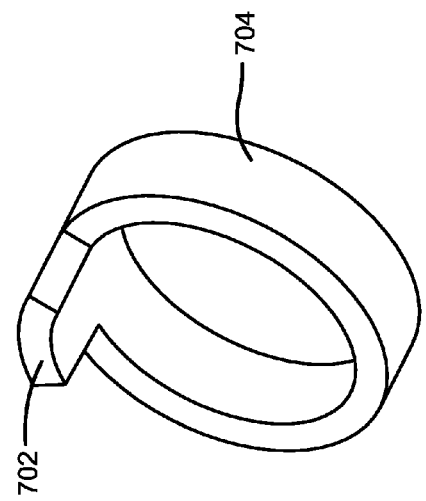
FIGS. 10A, 10B, 10C, and 10D are component diagrams illustrating various views of an example implementation of one or more portions of one or more systems described herein.
Figure 10D:
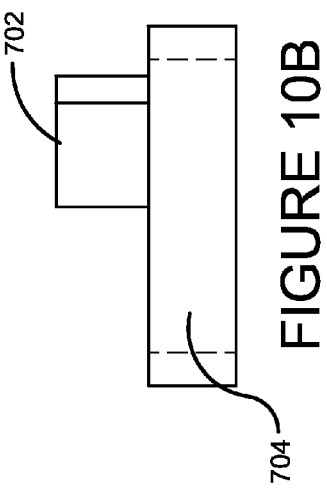
Figure 10A:
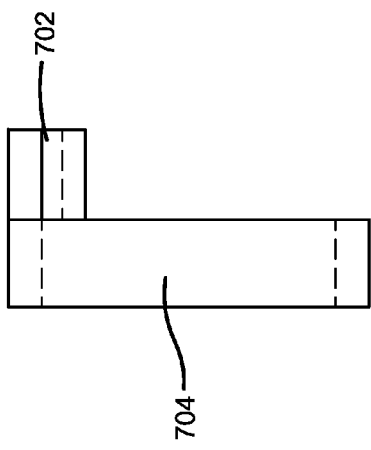
Figure 10B:
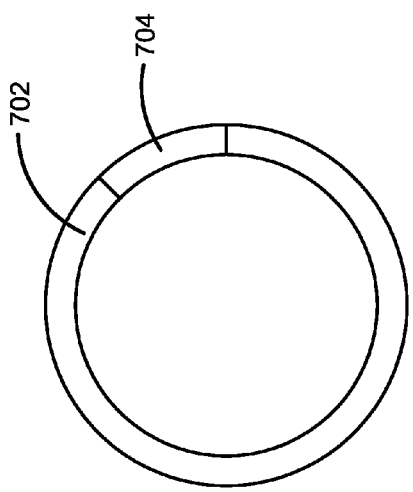
Figure 13B:
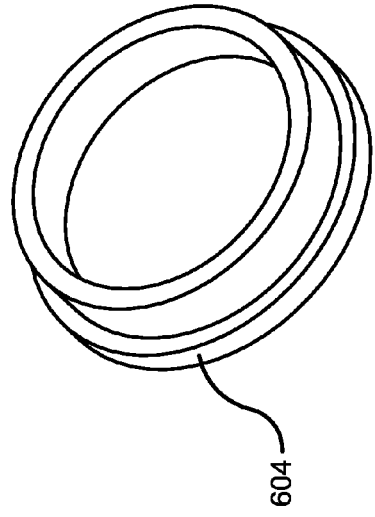
FIGS. 13A, 13B, and 13C are component diagrams illustrating various views of an example implementation of one or more portions of one or more systems described herein.
Figure 13C:
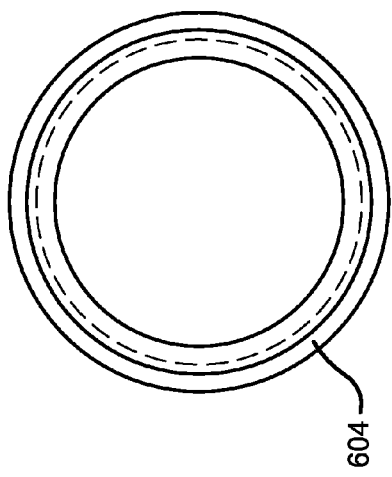
Figure 13A:
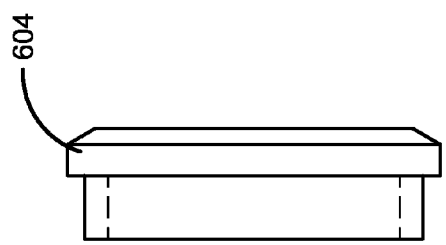

With reference to FIGS. 6-8, 12A-C, and 13A-C, and continued reference to FIGS. 3-5 and 9-11, a screw cap 604 may be operatively coupled with the fastener 302, for example, with the magnet component 602 positioned therebetween, as illustrated in FIGS. 6 and 7. In one implementation, the screw shank 402 may comprise a blunt end disposed at an end portion of the threaded portion 404. The blunt end may be engaged with the screw cap 604, such as by pressure fitting. As one example, the blunt end engaged with the screw cap 604 may be configured to apply pressure to a rod 304 inserted into the rod holder 308 (e.g., when the threaded portion is tightened down), such that the rod 304 may be secured (e.g., to a desired tensioning force) within the rod receiving shaft 506 of the rod holder 308.

Figure 5:
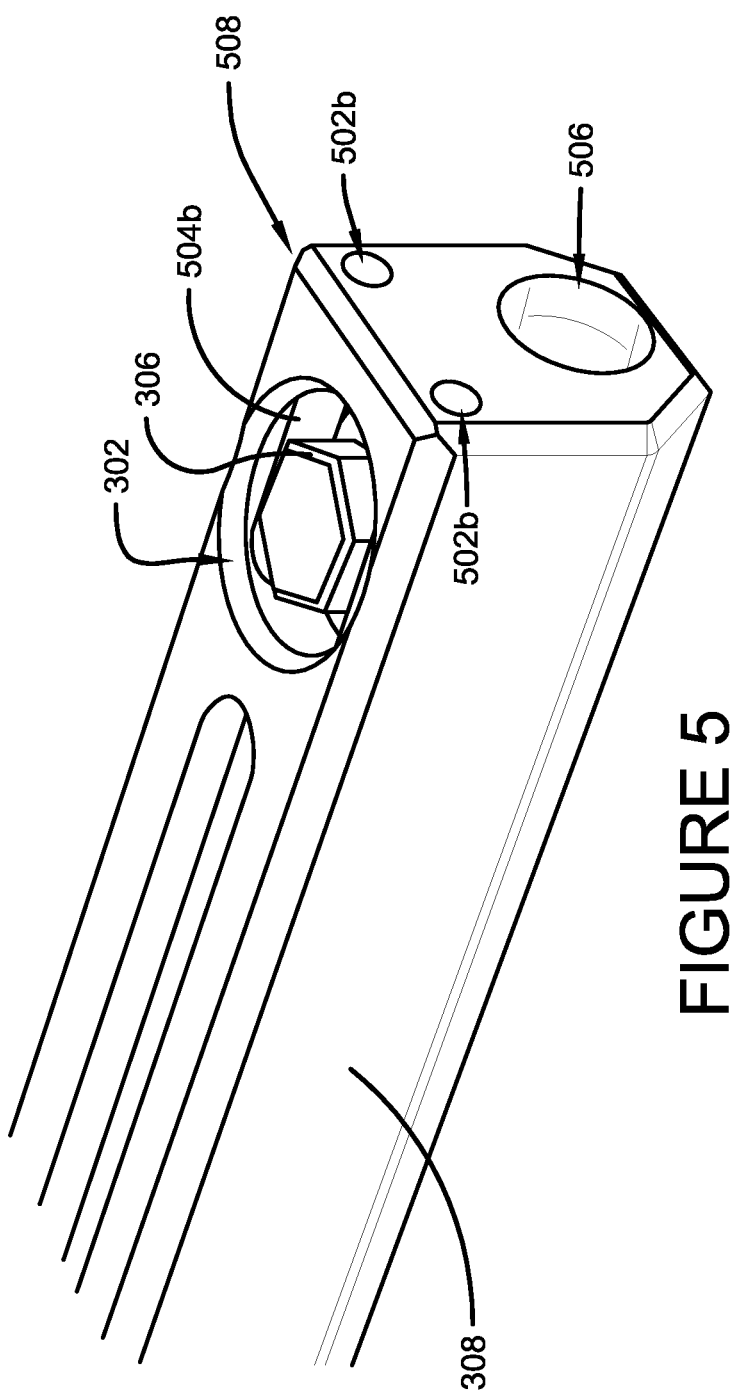
FIG. 5 is a component diagram illustrating a perspective view of an example implementation of one or more portions of one or more systems described herein.

As illustrated in FIGS. 5-7, a first screw stop component 508a may disposed in the first end 310, and/or a second screw stop component 508b may disposed in the second end 312 of the rod holder 308. The screw stop component 508 may be configured to mitigate over-rotation of the fastener 302, past a desired setting. The screw stop component 508 can comprise a stop receiver 502, comprising a tube disposed in the rod holder, and a stop pin 504, configured to be selectively engaged with the stop receiver 502. As one example, the stop pin 504 may be inserted into the stop receiver 502 after the fastener 302 is inserted into a fastener receiving hole 802 of the rod holder 308. In this way, for example, as illustrated in FIG. 5, a portion of the screw head 306 may engage the stop pin 504 when the fastener 302 is loosened (e.g., rotated out), preventing the fastener 302 from rotating past the position of the stop pin 504.

As an example, the screw stop component 508 may mitigate inadvertently unscrewing the fastener completely from the fastener receiving hole 802, thereby becoming disengaged from the rod holder 308. The screw stop component 508 may comprise any mechanical stop chosen with sound engineering judgment. As an example, the screw stop component 508 may be internal to the rod holder 308, as illustrated in FIG. 5, and/or it may be external to the rod holder 308. In an alternative design, the screw stop component 508 may be integrated with the fastener 302 itself, and/or may be fastened to the interior or exterior of the fastener 302.

Figure 14:
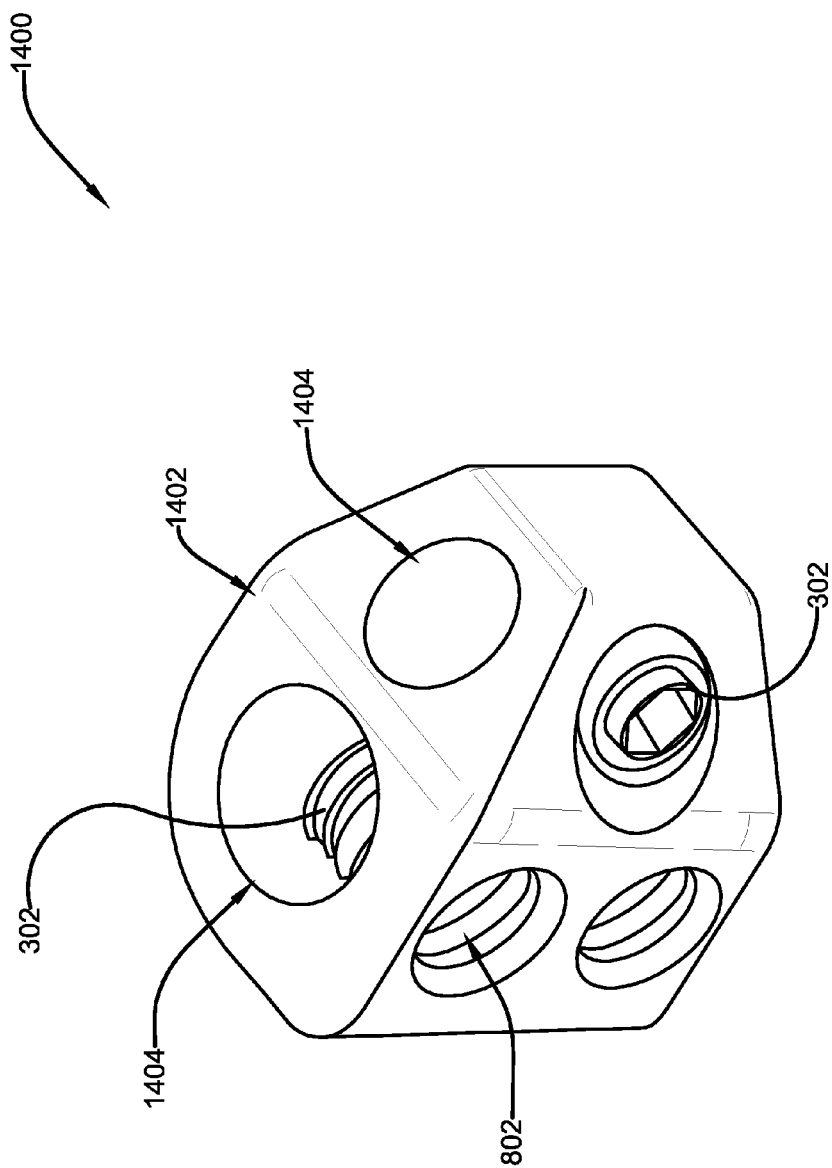
FIG. 14 is a component diagram illustrating a perspective view of an example implementation of one or more portions of one or more systems described herein.
Figure 15:
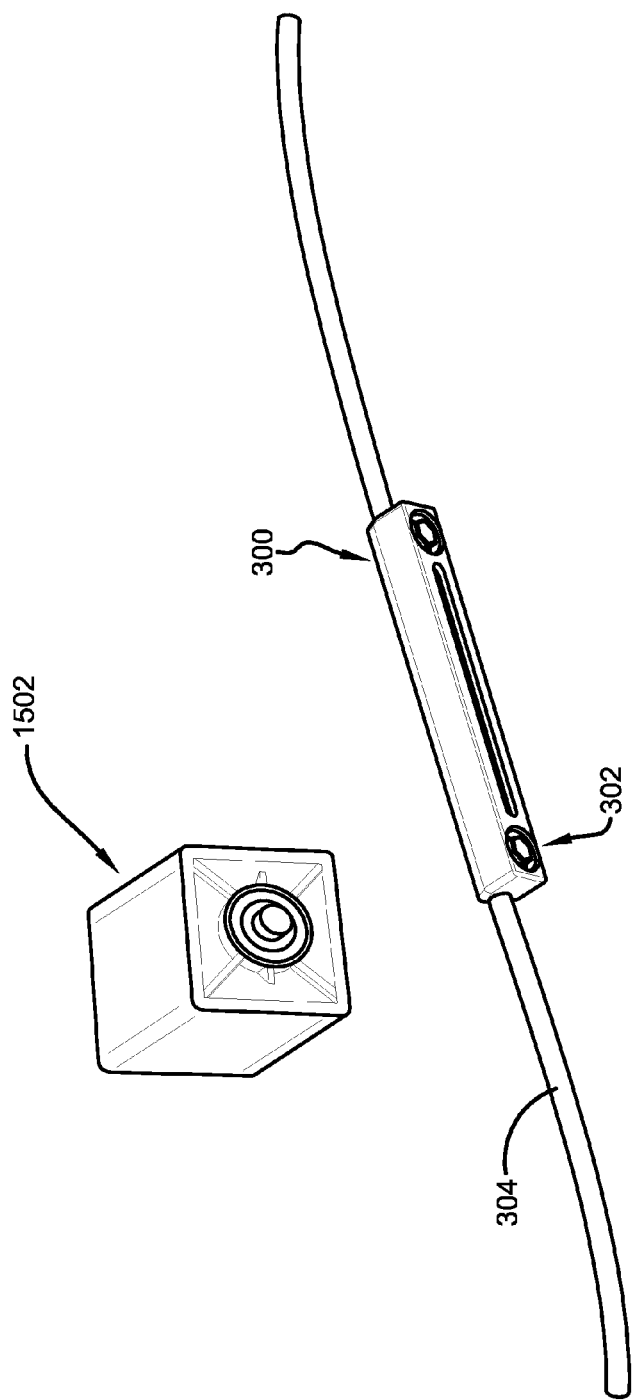
FIG. 15 is a component diagram illustrating a perspective view of an example implementation of one or more portions of one or more systems described herein.
Figure 16:
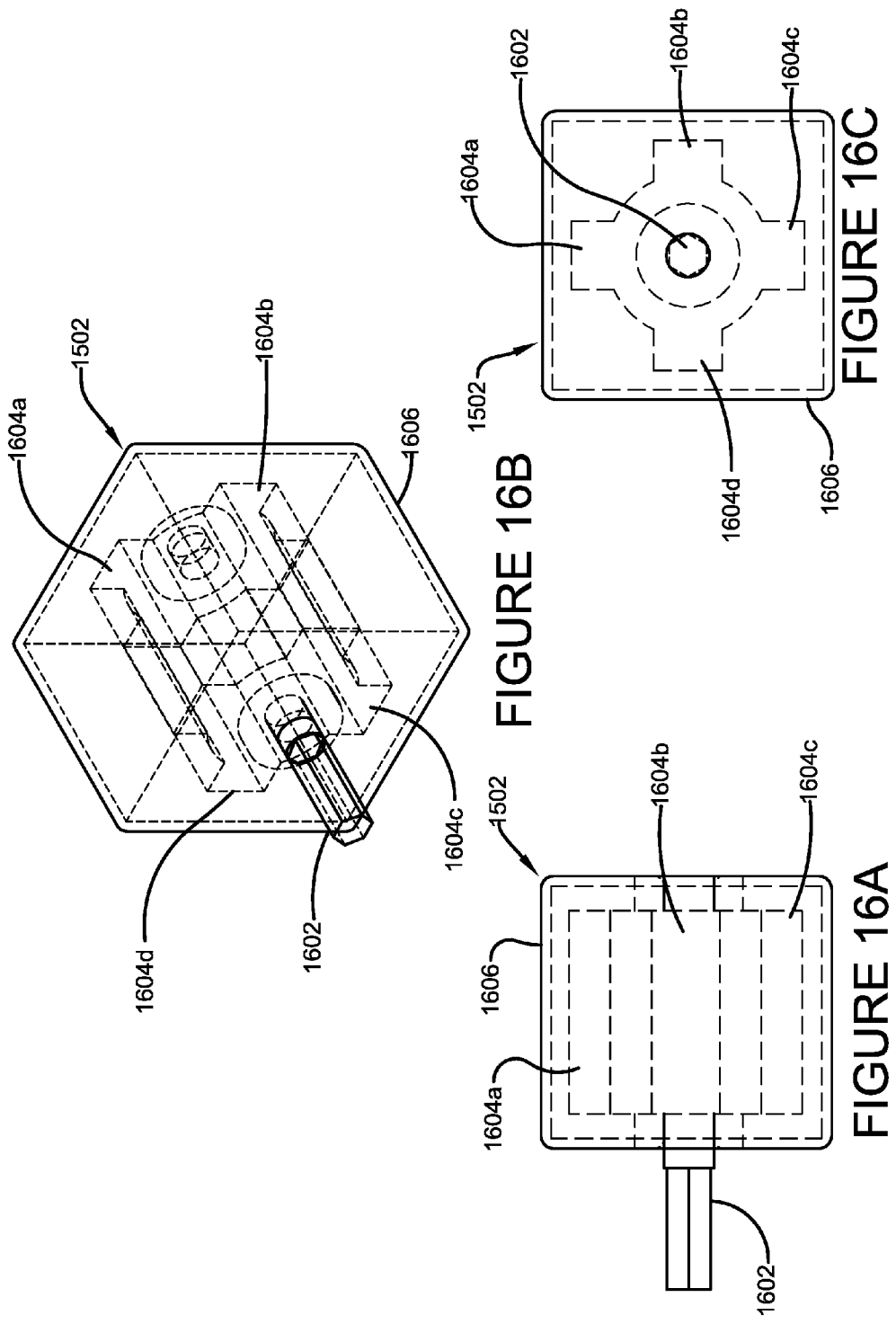
FIGS. 16A, 16B, and 16C are component diagrams illustrating various views of an example implementation of one or more portions of one or more systems described herein.
Figure 17:
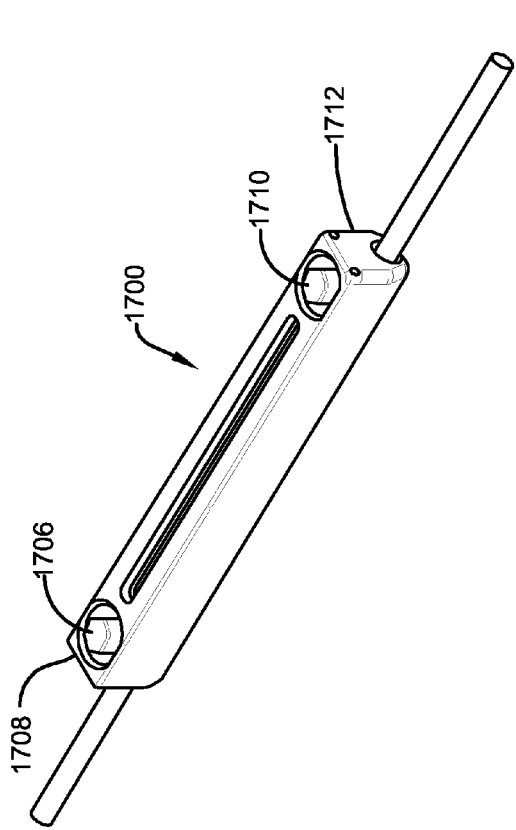
FIG. 17 is an example implementation of one or more portions of one or more systems described herein.
Figure 18:
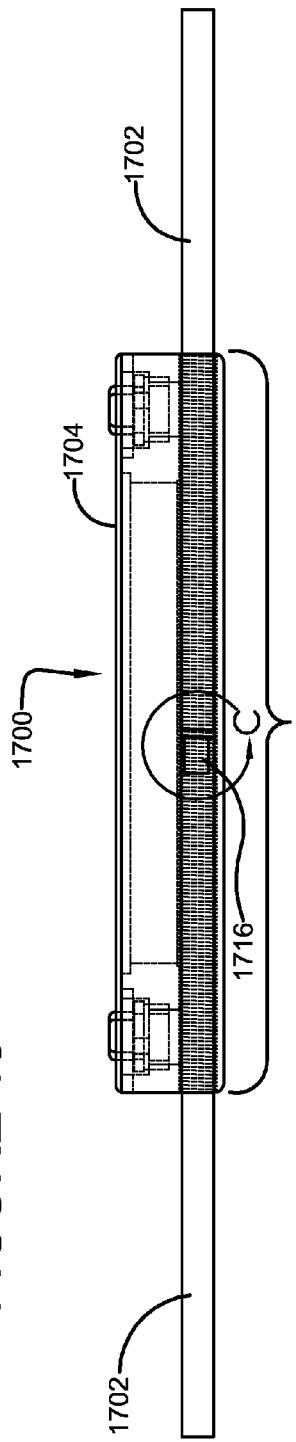
FIG. 18 is a cross sectional view of FIG. 17.
Figure 19:
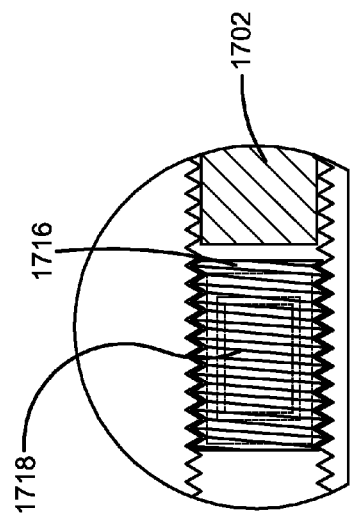
FIG. 19 is an enlarged view of a portion of FIG. 18.
Figure 20:
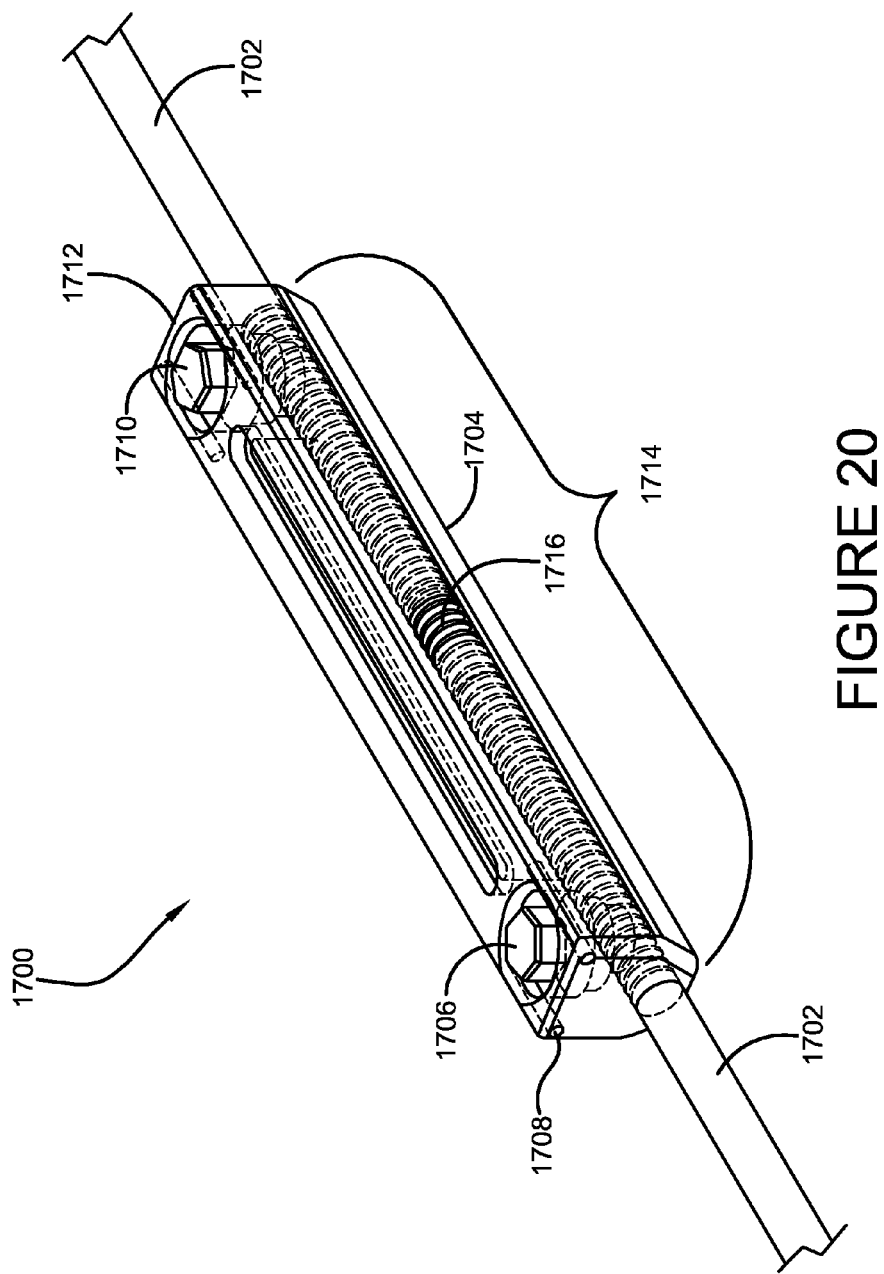
FIG. 20 is an example implementation of one or more portions of one or more systems described herein.

As illustrated in FIGS. 8 and 14, the rod holder 308 may comprise a first screw receiving hold 802a and a second screw receiving hold 802b. The screw receiving hole(s) may be configured to receive a fastener 302, such as a set screw. It is anticipated that alternate configurations of the rod holder/fastener configuration may be designed by those skilled in the art. As an example, in one implementation, a rod holder may comprise a type of rod clamp 1402, where a set screw-type fastener 302 may be utilized to secure one or more rods in respective rod holding shafts 1404.

In one implementation, one or more portions of the fastener 302 and/or fastener receiving hole 802 may be encapsulated with a suitable (e.g., medically inert) material. In one implementation, the magnet component 602 can be encapsulated within fastener 302, for example, to mitigate corrosion of the magnet component 602. As one example, the screw cap 604 may seal the magnet component 602 inside the interior portion 902 of the screw shank 402. In one implementation, encapsulation of the entire non-invasive tensioning device 300 may mitigate formation of undesirable materials on working parts of the device 300, for example, which may interfere with the ability of the threaded portion 404 to effectively engage with the screw receiving hold 802 of the rod holder 308.

With continued reference to FIGS. 3-14, a first fastener 302a may be inserted in a first screw receiving hole 802a, and a second fastener 302b may be inserted into a second screw receiving hold 802b. In one implementation, the first and/or second fasteners 302 may comprise set screws, for example, where a set screw may comprise a flat or relatively blunt end, configured to engage a rod 304, to secure the rod 304 against the rod holder 308 using pressure. In one implementation, the set screw may comprise a pointed or relatively pointed end, configured to engage an indentation, hole, valley, notch, or other set screw receiving cut-out, of the rod 304.

As one example, the rod 304 may comprise a plurality of rod positioning elements (e.g., indentations, holes, valleys, notches, etc.) respectively configured to facilitate securing of the rod with respect to said rod holder at a desired position. For example, the rod positioning elements may be disposed at locations along the rod suitable for adjusting the rod with respect to the desired scoliosis treatment. As another example, the respective one or more rods (e.g., 304a, 304b) may comprise a plurality of indentations respectively disposed at a desired interval, and/or a plurality of rises respectively disposed at a desired interval, where the indentations and/or valleys between the rises may selectively engage the set screw, and help secure the rod 304 in the rod holder 308.

In another implementation, of the present invention, the rod 304 may comprise one or more teeth that are configured to engage corresponding teeth disposed in the rod holder 308. As one example, the teeth on the rod 304 may engage the teeth in the rod holder 308 to provide a type of ratcheting adjustment system, where the rod may be selectively adjusted according to desired ratcheting positions of the teeth.

With continued reference to FIGS. 3-14, in one implementation, after the respective one or more fasteners are engaged with the rod holder 308 (e.g., screwed into the rod holder), a first stop pin 504a may be engaged with (e.g., inserted into) a first stop receiver 504a, and/or a second stop pin 504b may be engaged with a second stop receiver 504b. In this way, as described above, the fastener(s) may not be inadvertently disengaged from the rod holder 308.

A first growing rod 304a may be inserted into the first rod receiving shaft 506a of the rod holder 308, and a second growing rod 304a may be inserted into the second rod receiving shaft 506b of the rod holder 308. In one implementation, as described above, the first and/or second growing rods 304 may be selectively fastened to bone, such as a portion of the spine and/or ribcage. Further, in one implementation, the rod holder 308 may be selectively fastened to bone (e.g., in a human), for example, such as using the rod clamp of FIG. 14. As an example, after fastening the non-invasive tensioning device 300 to the bones, the patient may be surgically closed.

With reference to FIGS. 15 and 16A-C, and continued reference to FIGS. 3-14, in order to make an adjustment to the non-invasive tensioning device 300, which may have been surgically implanted in the patient, the rod holding fasteners 302 may need to be loosened. In order to turn the fasteners 302 without invasive surgery, a magnetic field generation component 1502 may be utilized. The magnetic field generation component 1502 can comprise one or more actuation magnets 1604, and an axle 1602 operably coupled with the one or more actuation magnets 1604. The axle 1602 may be configured to cause the actuation magnet(s) 1604 to rotate around an axis of magnet rotation to generate the desired magnetic field. As one example, the rotating magnets can provide the magnetic force needed to rotate the fastener, when brought in close proximity to the magnet component 602 disposed in the fastener 302.

As one example, a first actuation magnet 1604a may comprise a north pole disposed its outward facing end, a second actuation magnet 1604b may comprise a south pole disposed its outward facing end, a third actuation magnet 1604c may comprise a north pole disposed its outward facing end, and a fourth actuation magnet 1604d may comprise a south pole disposed its outward facing end. In this example, when the axle 1602 is rotated, an alternating north-south magnetic force may be provided at a face of the magnetic field generation component 1502. For example, the magnetic field generation component 1502 can comprise a housing 1606, a face of which may be placed proximate to a location of a fastener 302 in the non-invasive tensioning device 300 disposed in the patient. When activated (e.g., rotated in a desired direction), the alternating north-south magnetic force can be provided at the housing face, which may cause the fastener 302 to rotate (e.g., non-invasively), as described above.

Further, in one implementation, the one or more magnets 1604 of the magnetic field generation component 1502 can be rotated in a first direction (e.g., clockwise), for example, causing rotational torque to be applied to a fastener 302 in the first direction. In this implementation, the one or more magnets 1604 of the magnetic field generation component 1502 can be rotated in a second direction (e.g., counter-clockwise), for example, causing rotational torque to be applied to the fastener 302 in the second direction.

Additionally, an orientation of the magnetic field generation component 1502 with respect to a rotating magnetic component, disposed adjacent, (e.g., a fastener) may determine whether the adjacent rotating magnetic component is affected by the resulting magnetic field. For example, where two rotating magnetic components are disposed relatively perpendicular to each other (e.g., disposed on a growing rod apparatus in a patient), placing the magnetic field generation component 1502 in a first orientation, with respect to the rotating magnetic components, may cause rotational torque to be applied to merely a first one of the rotating magnetic components. In this example, placing the magnetic field generation component 1502 in a second orientation, with respect to the rotating magnetic components, may cause rotational torque to be applied to merely a second one or the rotating magnetic components, and not to the first. In this way, for example, if a physician wishes to loosen (e.g., or tighten) only one fastener at a time, an appropriate orientation of the magnetic field generation component 1502 may be used such that the desired fastener is affected by the resulting magnetic field, and not non-desired fasteners.

In one aspect, the action of the magnetic force from the magnetic field generation component 1502 can produce a hammering force, as described above. In one implementation, the magnet component 602 may rotate in a one to one revolution relative to the screw shank 402 and threaded portion 404 until rotational resistance is encountered, such as from a tightening against the growing rod 304, or against the screw stop component 508. In this implementation, for example, when rotational resistance is encountered, the magnet component 602 may not rotate at the same speed as the screw shank 402 and threaded portion 404. That is, for example, the magnets component 602 may have a greater velocity than the screw shank 402. In this example, respective turns of the magnet component 602 may attempt to rotate the screw shank 402 one revolution. However, if rotational resistance is encountered, the fastener 302 may not turn an entire revolution.

As an illustrative example, if a doctor determines that the tension of the growing rods 14 needs to be adjusted, the magnetic field generation component 1502 may be used to loosen the fastener(s) securing the one or more tensioning rods 304. In this example, the magnetic field generation component 1502 can be placed in close proximity to the patient, and rotated (e.g., manually or by a powered rotation source, such as a powered screwdriver, drill, etc.). Further, the rotation can be applied in a direction that causes the magnet component 602 to rotate (e.g., in a clockwise direction) within the fastener 302, in a fashion that produces torque, for example. As described above, the torque can cause the fastener 302 to rotate (e.g., loosen).

Additionally, in this example, after adjusting the patient into a desired position (e.g., moving the tensioning rod(s) 304 into and/or out of the rod holder 308), the respective fasteners may be re-tightened. As an example, the rotation of the magnetic field generation component 1502 can be reversed, thereby cause the fasteners to rotate in an opposite direction (e.g., counter-clockwise). In this example, the fastener 302 may rotate into the screw receiving hole 802 of the rod holder 308, at least until it contacts the growing rod 304. As described above, the hammering force provided by the magnet component 602 may cause the fastener to securely hold the rod 304 in the rod holder 308. In one implementation, non-invasive tensioning device may comprise a fastener locking component configured to mitigate loosening of the fastener 302 from secure engagement with the rod 304.

In one aspect, when the growing rods 14 are adjusted, means may be used to measure the change in position of the rods. In one implementation, in order to measure the distraction, any means chosen with sound engineering judgment may be applied. As one example, the use of beads (not shown) on the growing rods may be used, which can be detected using a non-invasive scan, such as CT scan, fluoroscopy, or other noninvasive means. In one implementation, electromagnetic means may be used to determine a distance of distraction, such as during adjustment. As one example, a sensing means (e.g., sensor device) may be implemented to determine a polarity change of a rotating magnetic component, such magnetic drive screw. In this implementation, for example, a polarity change of the rotating magnetic component may indicate particular amount of rotation (e.g., one rotation) of the rotating magnetic component. This may further indicate a distance traveled by combining the amount of rotation with a thread distance to determine how far the component travels per rotation, for example.

In one implementation, a control device may be used to limit an amount of rotation (e.g., and distance traveled) of the rotating magnetic component (e.g., fastener and/or drive screw), for example, by mitigating the effects of the magnetic force applied to the rotating magnetic component when a predetermined amount of rotation (e.g., and/or distance traveled) has been met. As one example, a physician may indicate that the magnetic drive screw can be adjusted by five millimeters. In this example, the control device may shut off the magnetic force generation component (e.g., or shield the magnetic drive screw from the magnetic force) upon the sensing means identifying that the magnetic drive screw has traveled the desired five millimeters. In this way, for example, the desired distraction may be applied, while mitigating a chance that the growing rods may be over or under distracted.

In another implementation of the present invention, the device 300 may be removed from the pediatric patient upon reaching orthopedic maturity such that a different implant system could be utilized to fuse the spine as needed. In such a case, for example, the device 300 may be adaptable such that the rotating magnet 36 will not need to be utilized to loosen it. The magnet 36 of the device may be loosened with a wrench or set screw driver and external surgical instruments to remove it and provides increased flexibility and adaptation to benefit the patient. One significant difference from the prior art is the absence of a drive mechanism inside the shaft 20. There is no complicated gearing, springs, batteries, or other components to operate the present invention.

The present invention while described in detail for application with scoliosis can be applied to a variety of orthopaedic applications including but not limited to, any application where set screws are utilized. Non-limiting examples may include the set screws being utilized in conjunction with bone plates, bone rods, or other screws. It can be used to treat a variety of conditions including without limitation, fractures or any bone deformity.

In another aspect, another implementation of an exemplary growth rod apparatus 1700 is shown in FIGS. 17-20. In this implementation, one or more growing rods 1702 may be adjusted by a device method similar to that described above, such as a magnetic field generation component (e.g., 1502 in FIG. 15). A rod holder 1704 may be provided (e.g., such as 308 of FIG. 3), for example, configured to hold the one or more growing rods 1702. A first magnet-based set screw 1706, such as described above (e.g., 302 of FIG. 3), may be rotationally engaged with a first end of the rod holder 1708, and configured to selectively engage the growing rod 1702, for example, when rotated down into the rod holder 1704. Further, a second magnet-based set screw 1710 (e.g., or a traditional set screw) may be rotationally engaged with a second end of the rod holder 1712, and configured to selectively engage the growing rod 1702, for example, when rotated down into the rod holder 1704.

In one implementation, a shaft portion 1714 of the rod holder 1704, which may be engaged with one or more of the growing rods 1702 can comprise internal threading (e.g., female threading). Further, a magnetic drive screw 1716 may be disposed in the shaft portion 1714. In one implementation, the magnetic drive screw 1716 may comprise a drive magnet 1718 (e.g., similar to 602 of FIG. 6) disposed therein. In one implementation, the drive magnet 1718 can be configured to be driven (e.g., rotated) using an external drive device, such as the magnetic field generation component described above (e.g., 1502 in FIG. 15), in a manner similar to that described above in FIGS. 2-16. That is, for example, a magnet collar (e.g., 702 of FIG. 7) may be fixedly attached to the drive magnet 1718, and the magnetic drive screw 1716 may comprise an internal magnet engaging component (e.g., 904 of FIG. 9A) disposed in opposing rotational engagement with the magnet collar of the drive magnet 1718. In this way, as described above, when an appropriate rotational magnetic force is applied to the magnetic drive screw 1716, the magnet collar of the drive magnet 1718 may apply rotational force to the magnet engaging component inside the magnetic drive screw 1716, for example, thereby causing the magnetic drive screw 1716 to rotate in accordance with the applied rotational magnetic force.

In one implementation, the magnetic drive screw 1716 may comprise external threading (e.g., male threading) that is configured to threadedly engage the internal threading of the shaft portion 1714 of the rod holder 1704. In this implementation, for example, magnetically rotating the magnetic drive screw 1716 may cause the magnetic drive screw 1716 to travel along the shaft portion 1714 of the rod holder 1704, with the direction of travel dependent upon a direction of rotation of the magnetic drive screw 1716 (e.g., and therefore the rotation and/or orientation of the magnetic force generation component 1502).

In one implementation, one or more of the growing rods 1702 may be engaged with the shaft portion 1714, for example, and secured in the rod holder 1704 by means of the first and/or second fasteners 1706, 1710. Further, in this implementation, when the growing rod 1702 is not secured to the rod holder 1704 (e.g., the fastener 1706 is loosened), the magnetic drive screw 1716 may be used to extend the growing rod 1702. For example, the magnetic drive screw 1716 can be magnetically rotated to cause the magnetic drive screw 1716 to engage an end of the growing rod 1702 disposed in the shaft portion 1714, such that the magnetic drive screw 1716 pushes at least a portion of the growing rod 1702 out of the shaft portion 1714. In this example, the fastener 1706 may then be tightened (e.g., magnetically) to secure the growing rod 1702 in the rod holder 1704 at a desired position.

As another example, when the magnetic drive screw 1716 is actuated, it is contemplated that the growing rod 1702 may translate in the rod holder 1704 between about 5 mm and about 20 mm per adjustment. For example, the one or more magnetic set screws 1706, 1710 can be loosened with the magnetic field generation component (e.g., 1502 in FIG. 15, in an appropriate orientation), which may cause the growing rod 1702 to loosen with respect to the rod holder 1704. Further, in this example, the magnetic field generation component can actuate the magnetic drive screw 1716, rotating the magnetic drive screw 1716 within the shaft portion 1714 of the rod holder 1704. The magnetic drive screw 1716 can apply force to the growing rod 1702, for example, thereby causing the growing rod 1702 to advance a desired distance in the rod holder 1704. In this example, once the desired adjustment is made, the one or more magnetic set screws 1706, 1710 may be tightened with the magnetic field generation component, securing the growing rod(s) 1702 in the rod holder 1704. Additionally, any devices and methodology chosen with sound engineering judgment may be utilized to obtain the desired distance of travel of the growing rod within the rod holder as long as the magnetic drive screw 1716 is directly or indirectly engaged with the growing rod 1702, and the drive magnet 1718 is actuated by the magnetic field generation component 1502.

The word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. Of course, those skilled in the art will recognize many modifications may be made to this configuration without departing from the scope or spirit of the claimed subject matter.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure.

In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

The implementations have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

What is claimed is:

1. A system for noninvasive tensioning, the system comprising:
   a rod holder member, the rod holder member having a body defining a first rod receiving shaft and defining a first fastener receiving opening, the first rod receiving shaft being configured to selectively receive an associated first rod therein, and the first fastener receiving opening intersecting the first rod receiving shaft within the rod holder body;
   an elongate first fastener defining a first longitudinal axis, the first fastener being threadedly engaged with the first fastener receiving opening, the first fastener being configured to be selectively rotated relative to the first fastener receiving opening to secure the associated first rod relative to the rod holder member; and
   an annular first magnetic component rotatably coupled on the elongate first fastener, the first magnetic component comprising a collar extension portion configured to selectively engage a corresponding magnetic engaging portion of the first fastener, the first magnetic component being movable about the first longitudinal axis of the first fastener under an influence of an associated external magnetic force to cause selective engagement between the collar extension portion of the first magnetic component and the magnetic engaging portion of the first fastener for applying torque to the first fastener to cause the associated first rod to be secured relative to the rod holder member.

2. The system of claim 1, further comprising: a second fastener comprising a second longitudinal axis, the second fastener being threadedly engaged with a second fastener receiving opening, the second fastener being configured to be selectively rotated relative to the second fastener receiving opening to secure an associated second rod relative to the rod holder member.

3. The system of claim 1, further comprising a first fastener locking component configured to mitigate loosening of the first fastener from engagement with the rod holder member.

4. The system of claim 1, the first rod comprising a plurality of rod positioning elements respectively configured to facilitate securing of the first rod with respect to the rod holder member at a desired position.

5. The system according to claim 1, wherein the selective engagement between the collar extension portion of the first magnetic component and the magnetic engaging portion of the first fastener is a selective hammering engagement between the collar extension portion of the first magnetic component and the magnetic engaging portion of the first fastener.

6. The system according to claim 1, wherein the first fastener receiving opening and the first rod receiving shaft mutually intersect substantially perpendicularly within the body of the rod holder member.

7. The system of claim 1, wherein one or more of:
the first rod is configured to be selectively engaged with one or more portions of an associated bone; and
the rod holder member is configured to be selectively engaged with one or more portions of the associated bone.

8. The system of claim 1, further comprising a magnetic field generation component configured to generate an associated and desired magnetic field, and comprising one or more of:
one or more actuation magnets; and
an axle operably coupled with the one or more actuation magnets, the axle configured to cause the one or more actuation magnets to rotate around an axis of magnet rotation to generate the desired magnetic field.

9. A system for noninvasive tensioning, comprising:
a rod holder member comprising a first end and a second end oppositely disposed from the first end, the rod holder member having a longitudinal axis extending from the first end to the second end, the rod holder member having a receiving shaft at least partially defined therein, the first end having a first opening, the rod holder member configured to selectively engage with one of one or more rods through the receiving shaft, the one of one or more rods having a secured position and an adjustable position;
a first fastener having a first threadably engageable end and a second nonthreadably engageable second end, the first fastener selectively engageable with the first opening at the first end along a first axis, the first axis intersecting the longitudinal axis of the rod holder member, the first threadably engageable end of the first fastener is configured to secure the one or more rods in the secured position with respect to the rod holder, the one or more rods being in the adjustable position when the fastener is not in a secured position; and
a first magnet component, rotatably disposed inside the second nonthreadably engageable second end of the first fastener, the first magnet component applying torque to the second nonthreadably engageable second end of the first fastener when subjected to a desired magnetic field, resulting in the first threadably engageable end of the first fastener rotating to secure the one or more rods in the secured position with respect to the rod holder.

10. The system of claim 9, further comprising a stop component operatively connected to the rod holder member to mitigate disengagement of the first fastener from the rod holder member.

11. The system of claim 9, comprising a second fastener having a first threadably engagable end and a second nonthreadably engagable second end, the second fastener selectively engagable with a second opening defined proximate the second end of the rod holder member, the second fastener having a first axis, the first axis of the second fastener intersecting the longitudinal axis of the rod holder member, the second fastener configured to secure one of the one or more rods in the secured position with respect to the rod holder, one of the one or more rods being in the adjustable position when the second fastener is not in a secured position; and
a second magnet component, operably coupled with the second nonthreadably engagable second end of the second fastener, and configured to apply torque to the second fastener when subjected to a desired magnetic field.

* * * * *